United States Patent [19]

Whaley et al.

[11] Patent Number: 5,499,540

[45] Date of Patent: Mar. 19, 1996

[54] ELECTROMAGNETIC ACOUSTIC TRANSDUCER FOR BOLT TENSION AND LOAD MEASUREMENT

[75] Inventors: Hubert L. Whaley; Thomas Powers; Daniel T. MacLauchlan, all of Lynchburg, Va.

[73] Assignee: The Babcock & Wilcox Company, New Orleans, La.

[21] Appl. No.: 196,917

[22] Filed: Feb. 15, 1994

[51] Int. Cl.[6] ........................................ F16B 31/02
[52] U.S. Cl. ................................. 73/761; 73/597
[58] Field of Search ........................ 73/597, 761

[56] References Cited

U.S. PATENT DOCUMENTS

| | | | |
|---|---|---|---|
| 4,434,663 | 3/1984 | Peterson et al. | 73/643 |
| 4,522,071 | 6/1985 | Thompson | 73/597 |
| 4,777,824 | 10/1988 | Alers et al. | 73/643 |
| 4,846,001 | 6/1989 | Kibblewhite | 73/761 |
| 5,058,439 | 10/1991 | Carpenter | 73/761 |
| 5,154,081 | 10/1992 | Thompson et al. | 73/597 |
| 5,220,839 | 6/1993 | Peterson | 73/597 |

FOREIGN PATENT DOCUMENTS

| | | | |
|---|---|---|---|
| 55-134331 | 10/1980 | Japan | 73/761 |
| 63-286761 | 11/1988 | Japan | 73/597 |
| 2248824 | 10/1990 | Japan | 73/597 |

OTHER PUBLICATIONS

G. A. Budenkov, V. N. Kuyatkoskii, and Yu V. Petrov, "Oblique Radiation of Ultrasound by an Electromagnetic–Acoustical Method", *Defektoskopia*, No. 1, pp. 45–50, Jan.–Feb. 1973.

R&D Proposal #93–038 to U.S. Army Tank Command, Warren, Mich., Mar. 17, 1993, Proposal marked "Proprietary".

Same Proposal as in "A" to NASA—Kennedy Space Center, Apr. 7, 1993, Proposed marked Proprietary.

NASA Tech Briefs MSC–21786, admitted prior art.

A. C. Holt, B. Cummingham, G. C. Johnson, & D. Auslander, "Review of Progress in Quantitative Nondestructive Evaluation", Ed. by D. O. Thompson & D. E. Chementi (Plenum Press, New York 1987), vol. 6B, pp. 1549–1557.

A. C. Holt, B. Cummingham, & G. C. Johnson, "Review in Quantitative Nondestructive Evaluation", edited by D. O. Thompson and D. E. Chementi (Plenum Press, New York 1988), vol. 7B, pp. 1405–1412.

Fred R. Rollins, Jr., "International Advances in Nondestructive Testing" (Gordon and Breach Science Publishers, Inc. 1977), vol. 5, pp. 229–253.

*Primary Examiner*—Richard E. Chilcot, Jr.
*Assistant Examiner*—Max Noori
*Attorney, Agent, or Firm*—Daniel S. Kalka; Robert J. Edwards

[57] ABSTRACT

A device for measuring a load on a part such as a bolt, comprises a socket having walls defining an interior space wherein the socket engages the bolt for transmitting a load to the bolt. An electromagnetic acoustic transducer comprising a magnet and a coil is located in the interior space of the socket near the bolt. The coil provides a current while the magnet provides a magnetic field such that the magnet and the coil generate an ultrasonic signal within the bolt. A detector is used to detect and measure a change in the ultrasonic signal at the bolt.

12 Claims, 4 Drawing Sheets

ELECTROMAGNETIC ACOUSTIC TRANSDUCER FOR BOLT TENSION AND LOAD MEASUREMENT

BACKGROUND OF THE INVENTION

1. Field of the Invention

The present invention relates in general to ultrasonic transducers and in particular to a new and useful method using an electromagnetic acoustic transducer for measuring the load on a bolt.

2. Description of the Related Art

A desired preload on a bolt is usually achieved during assembly of a structure by applying a specified torque to the bolt. It has been demonstrated that 90% of the torque applied to the bolt during assembly is used to overcome frictional forces. Small fluctuations in these frictional forces for a given fixed applied torque result in large fluctuations in the preload to the bolt. In a study of bolt preload vs. applied torque for bolts used in the construction of the Space Shuttle Orbiter, a variation in bolt preload of more than a factor of two was reported for a given applied torque. Bolts having improper preloads can lead to catastrophic failure of critical components in a wide range of applications.

Accordingly, ultrasonic methods using transducers have been developed in an effort to provide improved bolt load measurement. For example, when it was discovered that bolts used in reactor vessel internals in nuclear power plants were failing due to improper preload, an ultrasonic method was developed for setting the preload using conventional ultrasonic transducers. This method was subsequently used in the replacement of these critical bolts in the nuclear power generation facilities.

According to this method, the bolt preload is set by a precise measurement of the ultrasonic time of flight over the length of the bolt before and after tightening. While this method provides much improved bolt preload measurements compared to torque measurements, significant errors are introduced when removing and reapplying a transducer to the head of the bolt.

Using conventional ultrasonic transducers, sound waves are transmitted and received from the bolt via a coupling fluid. Because the velocity of sound in the couplant is many times slower than that of the steel, which is used in the bolt, small variations in the couplant path length can cause large variations in the transit time of the ultrasonic signal. The uncertainty introduced by the couplant path has limited most conventional ultrasonic bolt load measurements to measuring the time of arrival difference between successive echoes which assumes that the couplant path transit time is identical for each echo. There would be several advantages for only using the first echo for ultrasonic bolt preload measurements. Primarily, the first echo is generally the largest, and less affected by lack of parallelism and flatness as compared to later echoes. For example, if the end of the bolt surface is at a small angle, $\theta$, with respect to the head of the bolt surface, the first echo arrives at the head of the bolt at an angle of $2\theta$ while the second echo arrives at an angle of $6\theta$. The main drawback to these methods is that the all important application of couplant and transducer to the head of the bolt makes the automation of conventional ultrasonic bolt preload measurements a difficult task.

SUMMARY OF THE INVENTION

The present invention pertains to a device for measuring a load on a part, such as a bolt, and comprises a socket having walls defining an interior space, wherein the socket engages the bolt for transmitting a load to the bolt. An electromagnetic acoustic transducer comprising a magnet and a coil is located in the interior space of the socket near the bolt. The coil induces eddy currents while the magnet provides a magnetic field such that the magnet and the coil together generate an ultrasonic signal directly in to the bolt. A detector is used to detect and measure a change in the transit time of the ultrasonic signal in the bolt.

The present invention also comprises a method for measuring a load on a part which comprises providing a socket and engaging the socket with the part such that the interior space of the socket is provided between the socket and the part. A magnetic field is generated in the interior space of the socket; and a current is provided in the interior space of the socket such that the current and the magnetic field produce an ultrasonic signal within the part. The ultrasonic signal at the part is monitored and changes in the ultrasonic signal are detected by a detector.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 1:
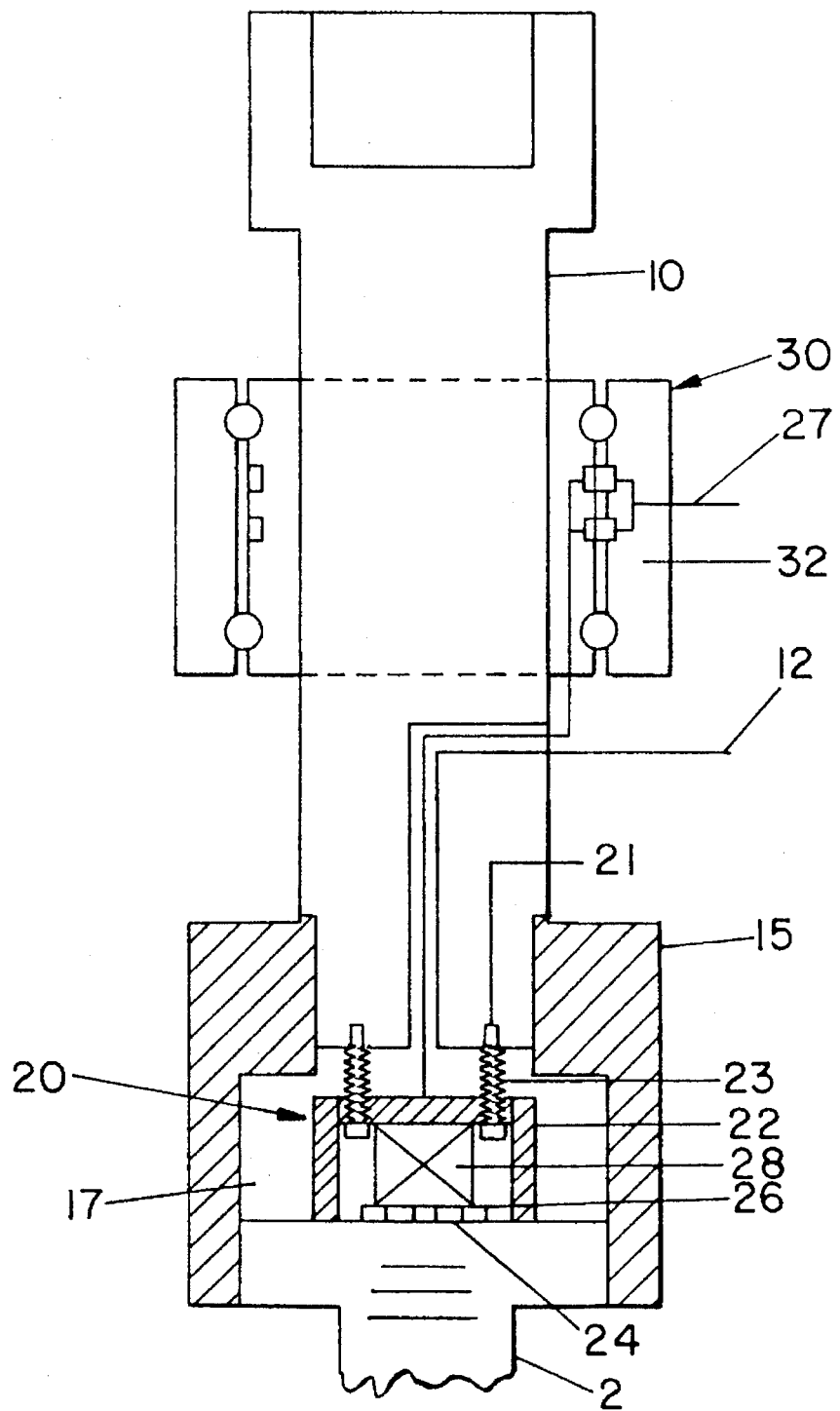
FIG. 1 is a schematic view illustrating the present invention.

The present invention is a device and method for tension and load measurement of a bolt using an electromagnetic acoustic transducer. The present invention comprises an electromagnetic acoustic transducer (EMAT) which generates and receives ultrasonic waves without the need to contact the material of a part, such as a bolt, in which the ultrasonic waves travel. The device according to the present invention, as shown in FIG. 1, is used in conjunction with a bolt 2 and comprises a socket 15 having an interior space 17. The socket 15 engages the bolt 2 for tensioning the bolt 2 and placing a load thereon. The interior space 17 of the socket 15 is located between the bolt 2 and the socket 15. A socket drive 10 is used in conjunction with the socket 15; and the socket drive 10 is detachably engagable with the socket 15 for changing to different size sockets for accommodating different sized bolts 2.

An electromagnetic transducer assembly 20 is located within the interior space 17 of the socket 15 at the bolt 2. The EMAT assembly 20 comprises a housing 22 and a wearplate 24 which contacts the bolt 2. Within the housing 22 and the wearplate 24 is located a permanent magnet 28 for producing a magnetic field and a coil 26 for providing a current. The EMAT assembly 20 is connected to the socket drive 10 by attachment bolts 21 and springs 23. A cable 27 is connected to the coil 26 for providing the current to the coil 26. The cable 27 is channeled to the coil 26 through a cable routing hole 12 located within the socket drive 10. The cable 27 is connected to the socket drive 10 by a slip ring assembly 30 engaged around the socket drive 10. The slip ring assembly 30 comprises slip ring brushes 32.

The electromagnetic transducer assembly 20 is used as a generator of ultrasonic waves by locating the coil 26 in a uniform magnetic field produced by the permanent magnet 28 such that the ultrasonic waves are provided near the surface of the metal bolt 2. By transformer action, a surface current is introduced into the metal bolt 2. This surface current in the presence of the magnetic field experiences a Lorentz force which produces oscillating surface stresses. On reception, the surface of the metal 2 oscillates in the magnetic field thereby inducing a voltage in the coil 26. The transduction process takes place within an electromagnetic skin depth, which for materials such as steel or aluminum, at megahertz frequencies, is a fraction of a mil.

The present invention provides a very reproducible non-contact system for generating and detecting ultrasound. Because the current of the EMAT coil 26 directly generates ultrasonic waves in the surface of the bolt 2, the precise time of flight measurements can be made by timing from the current pulse to the first reflection which eliminates many of the problems associated with known, conventional ultrasonic measuring devices.

Due to the development of the present invention, some of the problems that have been associated with previous efforts to measure bolt loading by ultrasonic methods have been minimized or eliminated. The EMAT of the present invention generates and receives ultrasonic waves without the need to contact the material in which the waves are traveling. This eliminates the requirement for a liquid couplant between the transducer and the material under test, which is the source of significant error and problems for automating the measurement process.

In operation, the EMAT sensor 20 rotates with the socket 15 and the bolt 2. Ultrasonic signals are transmitted and received via the slip rings 32 while testing the bolted joint 2. Alternatively, the transducer cable 27 is allowed to twist during the bolt tightening.

Figure 2:
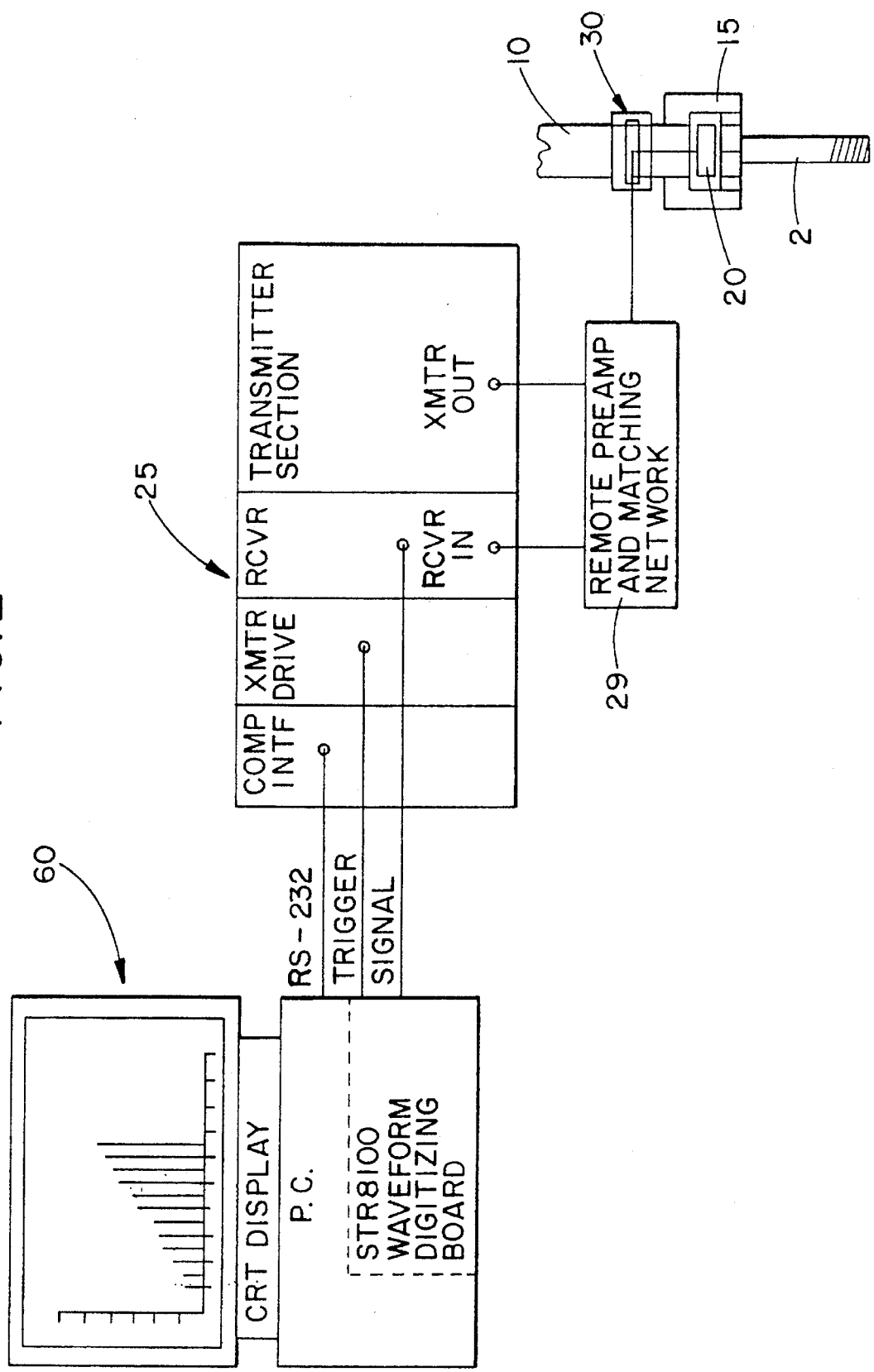
FIG. 2 is a schematic view illustrating the present invention used in conjunction with a detector and a monitor.

FIG. 2 shows EMAT instrumentation and computer 25 comprising a display means 60 and a remote amp and matching network 29 which electrically matches the EMAT coil 26 and cable 27 to the EMAT instrumentation 25. The detector 25, is a computer which takes measurements on the unloaded bolt 2 in order to establish a base line, and then measures and plots the bolt load while tightening the bolt 2.

As shown in FIG. 1, the EMAT sensor 20 is spring loaded by springs 23 so that the sensor 20 is automatically seated on the head of a bolt 2 as soon as the socket 15 is placed on the bolt head 2. The EMAT sensor 20 is attached to the drive assembly 10 in such a manner so that several different bolt sizes can be accommodated by changing sockets 15. EMAT measurements are taken as follows: prior to loading, i.e: on an unloaded bolt, continuously during the loading of the bolt, and after the loading of the bolt. When the desired load has been reached, the sensor 20 does not have to be removed. This eliminates the errors previously encountered in known transducers which are caused by having to attach and remove the ultrasonic transducers for the two tests, i.e. the preload test and the postload test. The method according to the present invention is well suited for automotive bolt tightening for use in production lines and various robotic applications.

It is well known that commercial ultrasonic bolt load measurement devices have been found to produce highly variable results primarily due to couplant variability.

Additionally, the repeatability of the EMAT method according to the present invention for measurements spaced over a period of time is much better than that of conventional ultrasonic methods. It may be desirable to measure the load of a bolt periodically to ensure that it is still within specifications. Because the EMAT 20 operates without couplant, re-application of the sensor 20 to make periodic measurements produces results with good accuracy if the load is unchanged.

Figure 3:
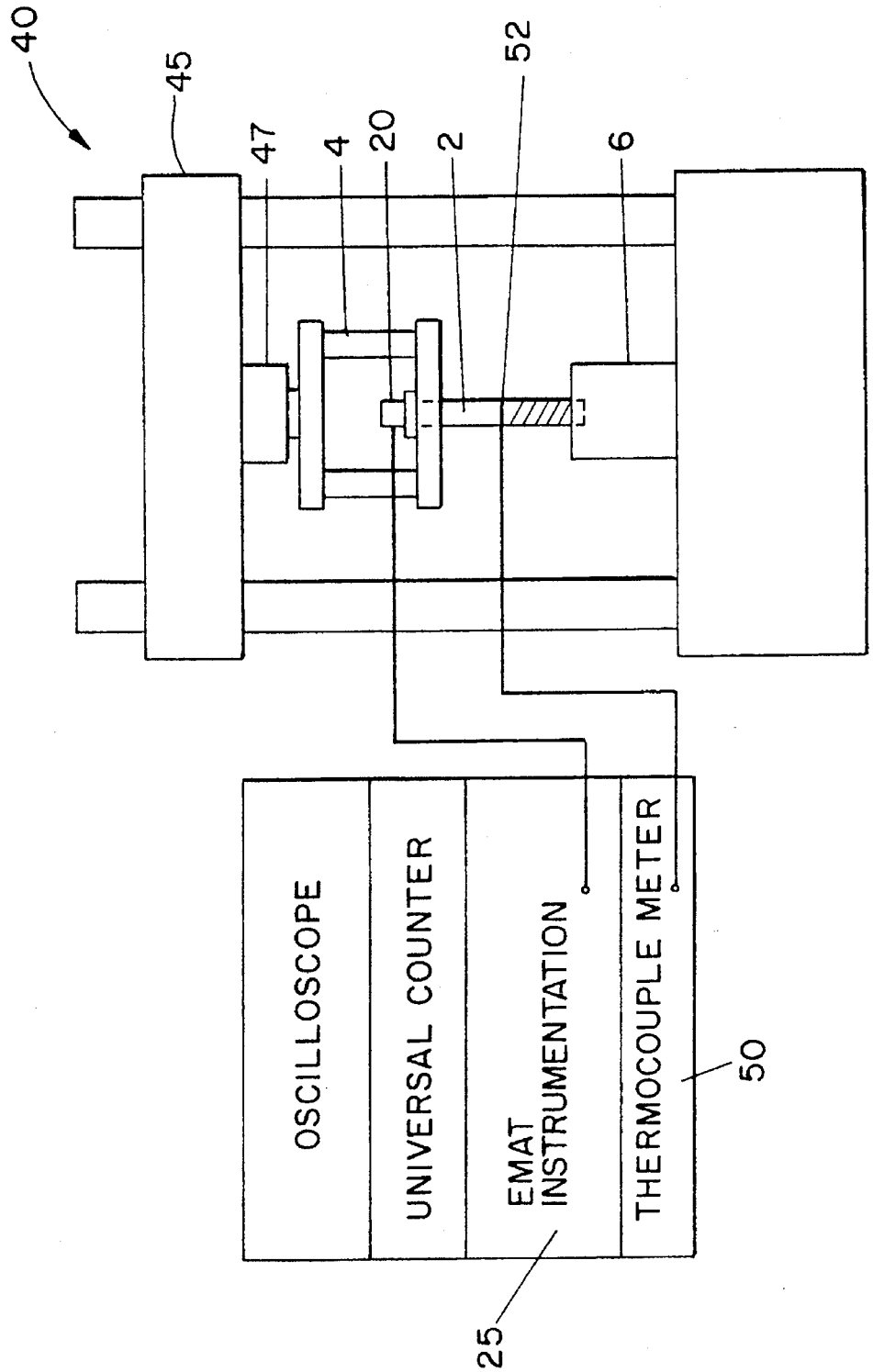
FIG. 3 is a schematic view illustrating a bolt tension test set-up utilizing the present invention.
Figure 4:
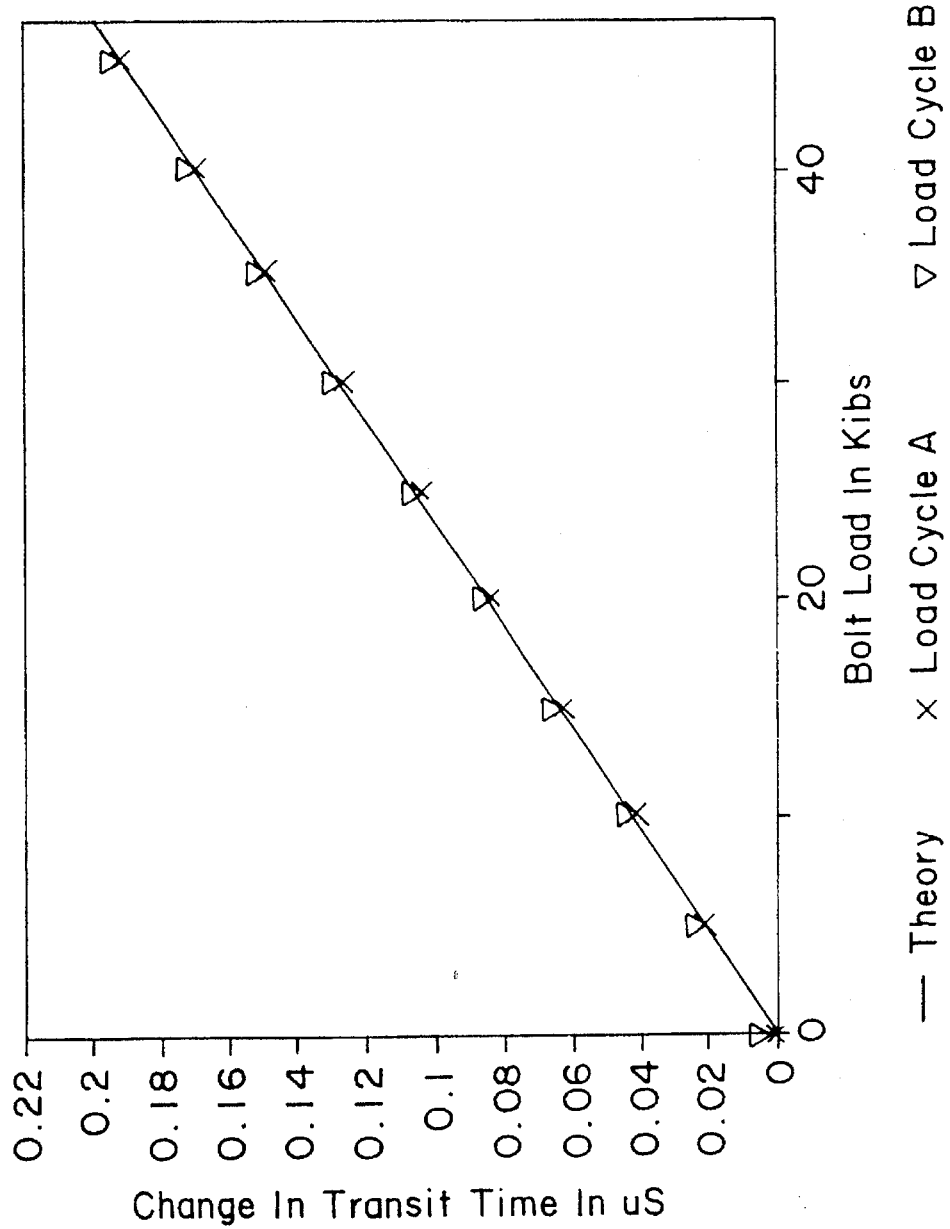
FIG. 4 is a graph plotting a change in transit time vs. bolt load.

A preliminary study of the novel concept of the present invention of using an EMAT for measuring bolt loading was first conducted under laboratory conditions. FIG. 3 shows an experimental set-up used during the preliminary study. The experimental set-up used a thermocouple meter 50 and associated hardware 52. A tension test set-up 40 was used in conjunction with a bolt loading fixtures 4 and 6 and a 50,000 pound loading frame comprising a load device 45. A specimen bolt 2 was loaded in the tension test set-up 40 at 5,000 pound increments and measurements of arrival time, load cell output, from load cell 47, and bolt temperature were recorded. The results of the measuring times for the transmitter current pulse to first echo are illustrated in FIG. 4 for two successive load cycles.

The effect on the accuracy of the readings caused by removing and replacing the transducer was tested by removing and replacing the transducer on the head of the unstressed bolt six times. The maximum variation in the time of flight was 4 nS. or an error corresponding to about 1.5% of the recommended load value. The average variation was only 1.2 nS. or less than 0.5% of the applied load. These results were unexpected since the experimental transducer was not very rugged and indicates that the transducer can be easily removed and replaced without introducing significant errors in bolt preload measurements. The ability to remove and replace the transducer without introducing significant errors allows for the reloading of a bolt in an assembly where preload can change.

While a specific embodiment of the invention has been shown and described in detail to illustrate the application of the principles of the invention, it will be understood that the invention may be embodied otherwise without departing from such principles.

What is claimed is:

1. A device for measuring a load on a part, the device comprising:

means for engaging the part, said engaging means having an interior space, the interior space of the engaging means being located between the engaging means and the part;

drive means for transmitting a load to the part through said engaging means, said drive means being detachably engagable with said engaging means;

a coil located in the interior space near the part for introducing an eddy current in the part;

means for providing current to said coin;

a magnet engaging the coil in the interior space and being attached to said drive means for providing a magnetic field, the magnet and the coil generating a noncontact ultrasonic signal in the part; and detection means for detecting a change in the ultrasonic signal provided to the part.

2. The device according to claim 1, wherein said engaging means comprises a socket.

3. The device according to claim 2, including a housing located in the interior space and a wearplate for contacting the part, the coil and the magnet being connected to the housing, and connecting means for connecting the housing to the drive means.

4. The device according to claim 3, wherein the connecting means comprises a bolt connected to the housing and the drive means.

5. The device according to claim 4, wherein the connecting means further comprises a spring between the housing and the drive means.

6. The device including according to claim 1, including a cable connected to the coil and the detection means.

7. The device according to claim 6, wherein the drive means includes an aperture for channeling the cable to the coil.

8. The device according to claim 7, including retaining means for electrically connecting the cable to the coil.

9. The device according to claim 8, wherein the retaining means comprises a slip ring assembly engaged with the drive means.

10. A method for measuring a load on a part, the method comprising the steps of:

providing a means for engaging a part, the engaging means having walls defining an interior space;

engaging the part such that the interior space is provided between the engaging means and the part;

transmitting a load to the part with drive means through the engaging means, the drive means being detachably engagable with the engaging means;

attaching a magnet with a coil to the drive means so that the magnet and coil are positioned in the interior space of the engaging means;

generating a magnetic field in the interior space of the engaging means;

providing a current in the interior space such that the current and the magnetic field produce a noncontact ultrasonic signal in the part;

monitoring the ultrasonic signal in the part; and detecting a change in the ultrasonic signal.

11. The method according to claim 10, wherein the engaging means comprises a socket.

12. The method according to claim 10, including rotating the socket and the part.

* * * * *